(12) United States Patent  
Vollmers et al.

(10) Patent No.: US 8,389,035 B1  
(45) Date of Patent: Mar. 5, 2013

(54) MEANS FOR EMITTING TERAHERTZ RADIATION

(75) Inventors: Cord R. Vollmers, Odessa, FL (US);  
Mark J. Hepp, Odessa, FL (US);  
Manfred Bauer, Odessa, FL (US)

(73) Assignee: MCM BioTechnologies, LLC, Odessa, FL (US)

( * ) Notice: Subject to any disclaimer, the term of this patent is extended or adjusted under 35 U.S.C. 154(b) by 577 days.

(21) Appl. No.: 12/462,879

(22) Filed: Aug. 11, 2009

(51) Int. Cl.  
*A21D 6/00* (2006.01)  
*A23C 3/00* (2006.01)  
*A23L 3/32* (2006.01)  
*C12H 1/06* (2006.01)  
*A61N 5/00* (2006.01)  
*G21G 5/00* (2006.01)

(52) U.S. Cl. .................................. 426/237; 250/492.1  
(58) Field of Classification Search .................. 426/241, 426/237  
See application file for complete search history.

(56) References Cited

FOREIGN PATENT DOCUMENTS  
WO    WO 2007101643 A1 *    9/2007

\* cited by examiner

*Primary Examiner* — Humera Sheikh  
*Assistant Examiner* — Tynesha McClain-Coleman  
(74) *Attorney, Agent, or Firm* — John Lezdey

(57) ABSTRACT

The present invention provides a method for imprinting water so as to emit Terahertz radiation and a method for maintaining the freshness of foodstuff with an article containing the imprinted water.

5 Claims, 2 Drawing Sheets

MEANS FOR EMITTING TERAHERTZ RADIATION

FIELD OF THE INVENTION

The present invention relates to methods and systems for altering the environment in closed chambers by the use of non-ionizing radiation that has been imprinted in water using a spectral region known as Terahertz Radiation. More particularly, there is provided a means for altering the environment so as to maintain the freshness of food products and retard the activity of bacteria associated with the food products.

BACKGROUND OF THE INVENTION

The use of magnets is known to create a magnetic field to energize water so as to permit the magnetized properties to dissipate to the surrounding areas.

U.S. Pat. No. 6,164,332 discloses an apparatus to deliver water energized by a vortex flow of water through a magnetic field.

U.S. Pat. No. 6,053,287 discloses a magnetic processing treatment facility for subjecting a fluid flow to magnetic energy that is integrated into an agricultural use to enhance activity in terms of crop growth and to increase the solubility of agricultural chemical agents to be used in a spray.

U.S. Pat. No. 6,602,411 discloses a magnetic treatment apparatus to "energize" water using at least two magnetic fields and an electrical current. The water is used to condition potable water, gardening water and recycled water.

U.S. Pat. No. 7,476,870 to Hopaluk et al, which is herein incorporated by reference, discloses a method of "energizing" water using reflected ultraviolet light.

There exists an AquaCharge® system for "energizing" water using paramagnetic material and Organite to clear harmful energy signatures from water. The system passes water through a concentrated paramagnetic system combined with quartz crystals in combination with orgone to provide the water with positive frequencies.

The article of Gerecht et al entitled "A Passive Heterodyne Hot Electron Bolometer Imager Operating at 850 GHz" in *IEEE Transactions on Microwave Theory and Technoques*, Vol 56, No. 5, May 2008, describes means for producing and detecting Terahertz radiation at a frequency of 720-930 GHz.

Light rays produced by the sun comprise electric and magnetic vibrations which are vibrating in more than one plane that is referred to as unpolarized light.

The spectrum of electromagnetic radiation striking the earth on a daily basis originates from the sun including for example commonly known spectra such as the visible and ultraviolet regions. The full spectrum is characterized by the term EOF representing the electro optical frequencies of solar radiation. The bands of these frequencies are characterized based upon wavelengths into nine general regions illustrated by the Solar Spectrum. These nine categories of increasing wavelength from 100 nm to 1 mm include Ultraviolet C, Ultraviolet B, Ultraviolet A, Visible light, Infrared A, Infrared B, Infrared C, FAR Infrared, and Extreme Far Infrared, the latter of which is part of the Terahertz spectrum.

This special region known as Terahertz spectrum radiation or the "Terahertz Gap" falls between electromagnetic frequencies (measured with antennas) and optical frequencies (measured with optical detectors). There are currently no known natural sources of Terahertz radiation in the Extreme Far Infrared region.

Terahertz radiation is a non-ionizing sub-millimeter radiation and shares with X-rays the capability to penetrate a wide variety of non conductive materials. Terahertz radiation can pass through clothing, paper, cardboard, wood, masonry and plastic. It can also penetrate fog and clouds, but cannot penetrate metal or water.

It is possible to transform unpolarized light into polarized light. Polarized light waves are light waves in which the vibrations occur in a single plane. The process of transforming unpolarized light into polarized light is known as polarization. There are a variety of methods of polarizing light. The most common method of polarization involves the use of a Polaroid filter. Polaroid filters are made of a special material which is capable of blocking one of the two planes of vibration of an electromagnetic wave. A Polaroid serves as a device which filters out one-half of the vibrations upon transmission of the light through the filter. When unpolarized light is transmitted through a Polaroid filter, it emerges with one-half the intensity and with vibrations in a single plane; it emerges as polarized light.

A Polaroid filter is able to polarize light because of the chemical composition of the filter material. The filter can be thought of as having long-chain molecules that are aligned within the filter in the same direction. During the fabrication of the filter, the long-chain molecules are stretched across the filter so that each molecule is aligned in the vertical direction. As unpolarized light strikes the filter, the portion of the waves vibrating in the vertical direction are absorbed by the filter. The general rule is that the electromagnetic vibrations which are in a direction parallel to the alignment of the molecules are absorbed.

The alignment of these molecules gives the filter a polarization axis. This polarization axis extends across the length of the filter and only allows vibrations of the electromagnetic wave that are parallel to the axis to pass through. Any vibrations which are perpendicular to the polarization axis are blocked by the filter. Thus, a Polaroid filter with its long-chain molecules aligned horizontally will have a polarization axis aligned vertically. Such a filter will block all horizontal vibrations and allow the vertical vibrations to be transmitted. On the other hand, a Polaroid filter with its long-c chain molecules aligned vertically will have a polarization axis aligned horizontally; this filter will block all vertical vibrations and allow the horizontal vibrations to be transmitted.

SUMMARY OF THE INVENTION

The present invention relates to a method and means for altering the environment in a closed system by non-ionizing Terahertz radiation emitted from water imprinted with wavelengths of 100 micrometers to 1 micrometers or frequencies from 300 GHz to 3 THz so as to reduce the activity of pathogens and maintain the freshness of food products. More particularly, there is provided water which has been imprinted with Terahertz non-ionizing in a geometrically suitable transparent container which emits radiation at least at a frequency of 720-930 GHz, preferably at 850 GHz into a closed environment containing food products.

Advantageously, the containers in which the food products are stored with the means for radiating the Terahertz non-ionizing radiation consists of refrigerators, coolers, food transports and the like.

The container storing the "energized" water is preferably egg shaped.

It is a general object of the invention to provide a means for generating non-ionizing radiation from a container to alter the environment in a storage container for foodstuff.

It is another object of the invention to reduce the pathogens associated with food by the use of Terahertz radiation and thereby extending the shelf life of the product.

It is yet another object of the invention to accelerate the conversion of glycogen in fruits and vegetables, such as apples and tomatoes, using Terahertz radiation.

It is a still further object of the invention to reduce oxidation and retain the moisture of food in the refrigerator or pantry without using chemicals.

It is a yet another object of the invention to provide a means for altering the environment in a closed chamber with Terahertz radiation so as to reduce pathogenic growth, mold and mildew.

These and other objects will become apparent from the reading of the description of preferred embodiments and the drawings.

DESCRIPTION OF THE PREFERRED EMBODIMENTS

According to the present invention, there is provided a means for radiating in a closed chamber Terahertz radiation and imprinting water containing inorganic salts and/or minerals with wavelengths of about 100 micrometers to 1 micrometer or frequencies from 300 GHz to 3 THz, preferably radiation at a frequency of about 720 to 930 GHz, most preferably of about 850 GHz which is placed in a geometrically suitable transparent container to effect the environment in the chamber. Preferably, the chamber is environmentally controlled.

Figure 1:
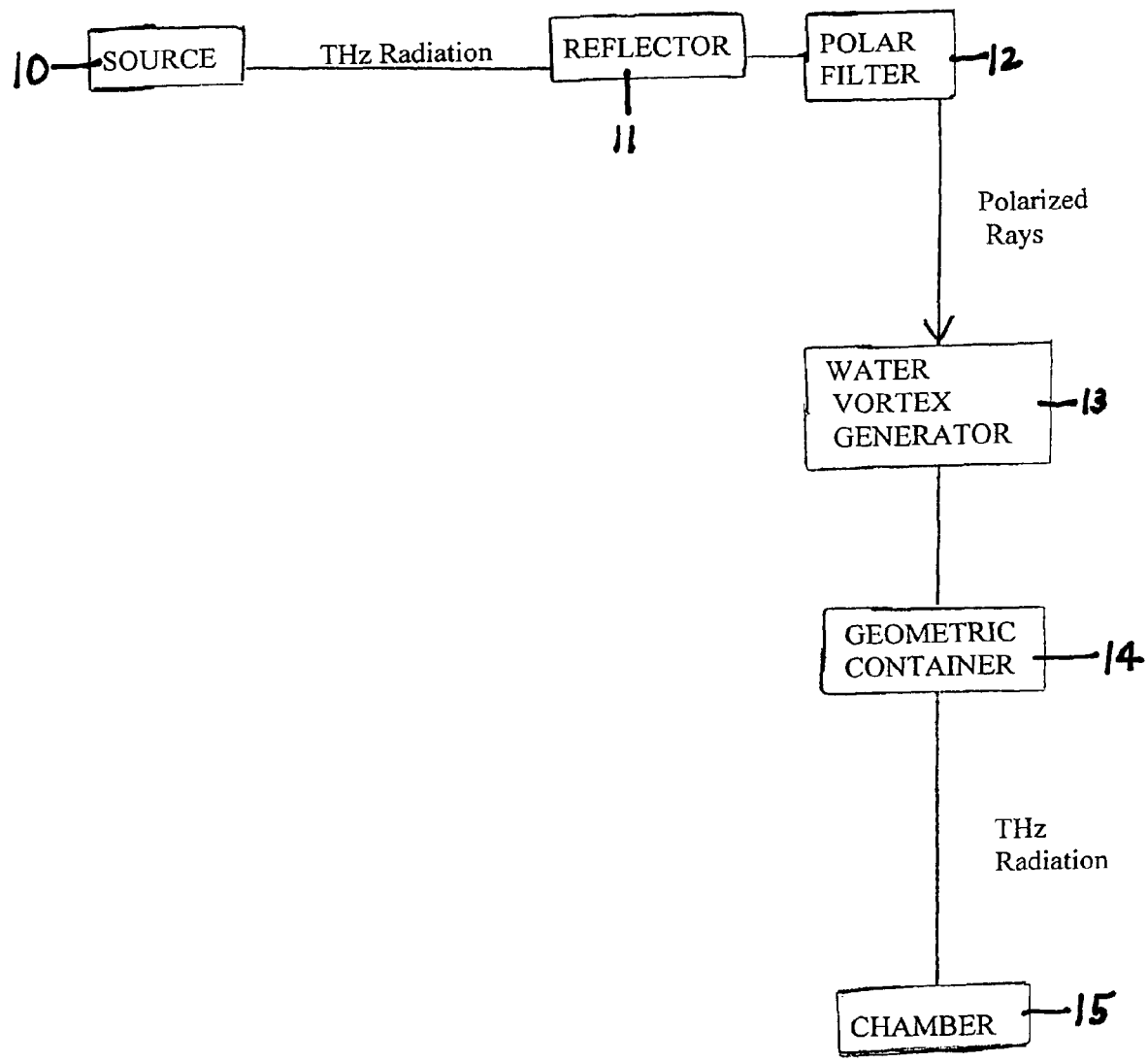
FIG. 1 is a block diagram of a procedure for preparing a means for generating Terahertz radiation to imprint water.

As seen in FIG. 1 of the drawing, a source (10) of Terahertz radiation which generates the desired Terahertz radiation, such as disclosed in aforementioned IEEE Transactions on Microwave Theory and Techniques or naturally from the sun, is beamed to a metal reflector (11). The electro-optical frequencies generated are reflected onto a polarization filter (12). The polarized rays are then directed into a tank containing ionized water (22) which contains inorganic salts and/or minerals to absorb the polarized Terahertz radiation and store imprinted information.

The tank of water contains a vortex generator (13) to create a spinning turbulent flow of water in the tank. The turbulence is produced for at least one hour in a tank containing about 125 liters of the polarized water. The irradiated polarized water is then rested for about one hour to allow imprinting of the Terahertz radiation. The vortex generated is preferably rotated in a counterclockwise direction.

The imprinted water can then be placed in a geometrically acceptable transparent container (14), for example, an egg shaped transparent container, which when placed into an environmentally controlled chamber (15) transmits the desired Terahertz radiation. The container can also be placed in a non controlled environment such as an insulated container.

When using sunlight as the source of Terahertz radiation, consideration is taken as to the amount of sunlight available. One of the properties of sunlight is its wave particle duality. The main property used in the process encompasses the particle aspect of the waves of sunlight. Using the high photonic energy of the unobstructed sunlight the polarized light has the ability to change the electromagnetic spin of the electrons in the water molecules containing the inorganic salts and/or minerals such as found in spring water. The process synchronizes the water molecules into certain formations allowing the water to absorb the Terahertz radiation, especially those in the Far Infrared end of the spectrum.

Figure 2:
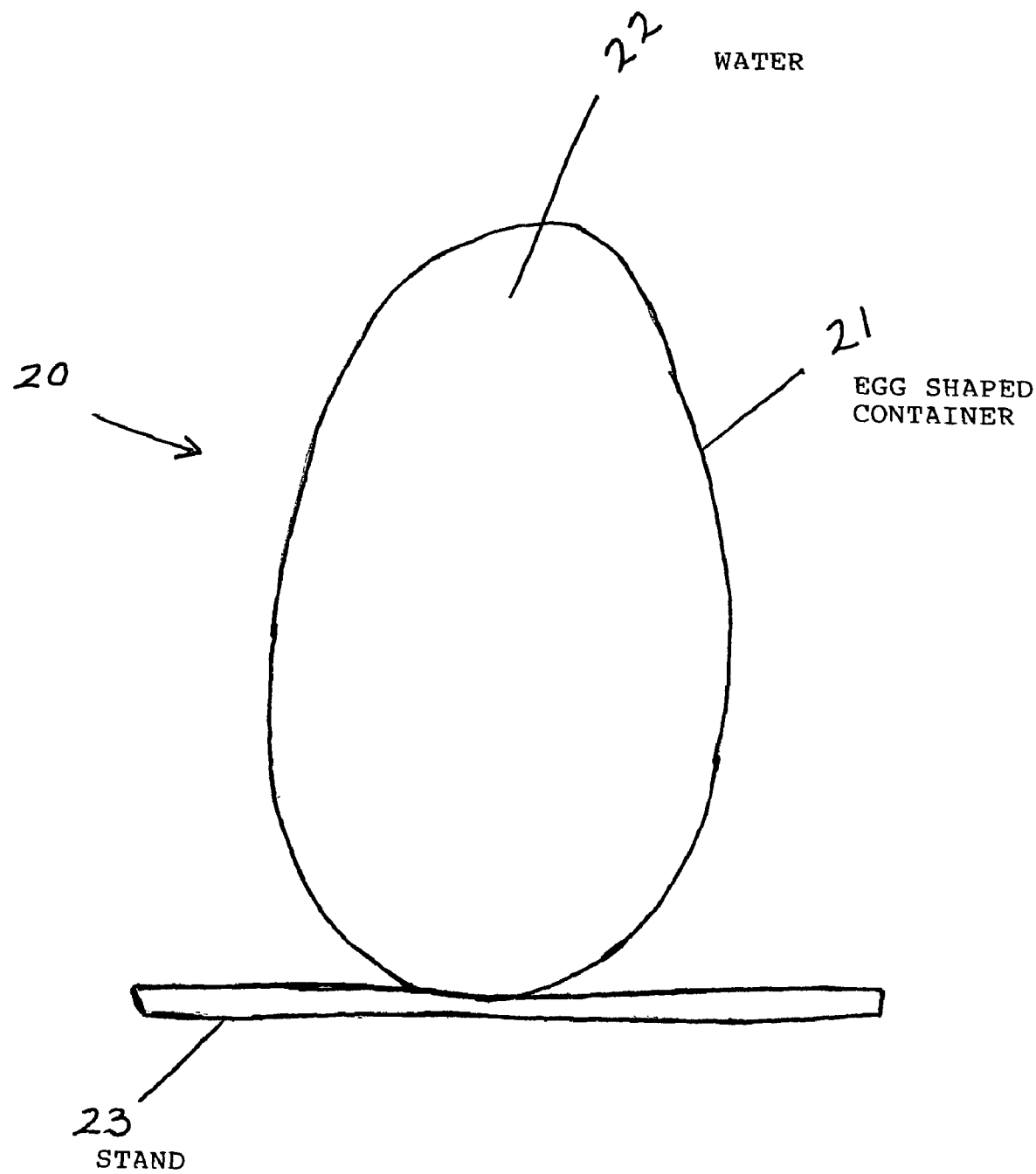
FIG. 2 represents a geometric container for storing the energized water of the process and emitting radiation in a closed chamber.

As seen in FIG. 2, proper geometrically shaped containers (20), for example, egg shaped transparent containers (21) containing the energized water (22) are placed on a stand (23). Proper geometrically shaped containers are well known to transmit various energies whereby the wavelengths do not interfere with each other. Containers which are egg shaped have this capability. Pyramid configurations are considered to channel energies in the proper direction as well. Tubular containers also permit the energizing properties of the water to dissipate therefrom in proper order.

Use of the radiation emitting devices of the invention can reduce oxidation and retain moisture in food that are stored in chambers such as refrigerators, refrigeration vehicles, coolers, pantries and the like which causes odors and food spoilage.

Example 1

A comparison study was made wherein three controlled environment chambers were used. One chamber contained 25 fresh picked Gala apples. A second chamber contained 25 fresh picked Gala apples treated with gaseous 1-methylcyclopropene (1-MCP) which is commercially available under the trademark Smart Fresh®. A third chamber contained 25 fresh picked Gala apples and the egg shaped device with the Terahertz radiation treated water of the invention.

After 6 weeks the apples were tested to firmness, acid levels, color, taste and aroma.

Results

The non-treated apples had soft spots, brown spots when sliced, tasted as being stale and not fresh. The color was only slightly faded.

The apples treated with 1-MCP were crunchy, fresh tasting and similar to the fresh picked apples.

The apples from the third chamber had the same quality and characteristics as the apples from the second chamber.

The terms and expressions which have been used are not limitations and there is no intention in the use of these terms and expressions of excluding any equivalents of the features shown and described or portions thereof, but recognize that various modifications are possible within the scope of the invention claimed.

What is claimed is:

1. A method for altering the environment in a closed system which comprises emitting Terahertz radiation from Terahertz radiation treated water containing members of the group consisting of soluble inorganic salts and minerals that have been imprinted with Terahertz wavelengths of about 100 micrometers to 1 micrometer and frequencies from 300 GHz to 3 THz by means of a polarizing filter through which said polarized radiation containing Terahertz, spectrum radiation passes onto the water.

2. The method of claim 1 wherein the radiated water is in a transparent container.

3. The method of claim 1 wherein said closed system is an environmentally controlled chamber.

4. The method of claim 1 wherein said closed system contains food stuff.

5. The method of claim 1 wherein the source of Terahertz radiation is from the sun.

* * * * *